United States Patent
Wang et al.

(10) Patent No.: US 11,766,665 B2
(45) Date of Patent: Sep. 26, 2023

(54) METHOD FOR EFFICIENTLY SYNTHESIZING PRIMARY AMINES

(71) Applicant: East China University of Science and Technology, Shanghai (CN)

(72) Inventors: Yanqin Wang, Shanghai (CN); Wanjun Guo, Shanghai (CN); Shuang Xiang, Shanghai (CN); Xiaohui Liu, Shanghai (CN); Yong Guo, Shanghai (CN)

(73) Assignee: East China University of Science and Technology, Shanghai (CN)

( * ) Notice: Subject to any disclaimer, the term of this patent is extended or adjusted under 35 U.S.C. 154(b) by 1 day.

(21) Appl. No.: 17/563,421

(22) Filed: Dec. 28, 2021

(65) Prior Publication Data

US 2023/0102416 A1 Mar. 30, 2023

(30) Foreign Application Priority Data

Sep. 30, 2021 (CN) .......................... 202111168819.5

(51) Int. Cl.
| | | |
|---|---|---|
| *C07C 209/78* | (2006.01) | |
| *B01J 23/75* | (2006.01) | |
| *B01J 23/78* | (2006.01) | |
| *B01J 23/83* | (2006.01) | |
| *B01J 23/882* | (2006.01) | |
| *B01J 35/00* | (2006.01) | |
| *B01J 37/03* | (2006.01) | |
| *B01J 37/08* | (2006.01) | |
| *B01J 37/18* | (2006.01) | |

(52) U.S. Cl.
CPC .............. *B01J 23/75* (2013.01); *B01J 23/78* (2013.01); *B01J 23/83* (2013.01); *B01J 23/882* (2013.01); *B01J 35/0006* (2013.01); *B01J 37/031* (2013.01); *B01J 37/082* (2013.01); *B01J 37/18* (2013.01); *C07C 209/78* (2013.01); *C07C 2601/08* (2017.05)

(58) Field of Classification Search
None
See application file for complete search history.

(56) References Cited

PUBLICATIONS

Gosselin et al. (J. Org. Chem., 2010, 75(12), 4154) (Year: 2010).*

* cited by examiner

*Primary Examiner* — Sudhakar Katakam
*Assistant Examiner* — Jennifer C Sawyer
(74) *Attorney, Agent, or Firm* — Westbridge IP LLC

(57) ABSTRACT

Disclosed is a method for efficiently synthesizing primary amines, which comprises using carbonyl compounds or alcohol compounds as reaction substrate, liquid ammonia or alcohol solutions of ammonia as nitrogen source, and hydrogen as hydrogen source, and reacting in reaction medium catalyzed by a cobalt-based catalyst to obtain the primary amines. Due to high catalytic activity, the method can realize the reductive amination of carbonyl compounds and the hydrogen-borrowing amination of alcohol compounds at low temperatures in a short time to obtain the primary amines with high yield, and is applicable to a wide range of substrates. The obtained primary amines can be used as raw materials with high extra value for producing polymers, medicines, dyes and surfactants. Further, the cobalt-based catalyst has a good industrial application prospect because it is magnetic which can facilitate separation and recycling of the catalyst. Moreover, the inexpensive cobalt-based catalyst can significantly reduce industrialization cost.

20 Claims, 1 Drawing Sheet

METHOD FOR EFFICIENTLY SYNTHESIZING PRIMARY AMINES

CROSS-REFERENCE TO RELATED APPLICATIONS

This application claims priority to and the benefit of Chinese Patent Application No. CN202111168819.5 filed Sep. 30, 2021 and entitled "Method for Efficiently Synthesizing Primary Amines," the disclosure of which is incorporated herein by reference in its entirety.

TECHNICAL FIELD

The present disclosure relates to the technical field of industrial synthesis, and in particular to a method for efficiently synthesizing primary amines.

BACKGROUND

Currently, the general industrial route for the synthesis of primary amines is the direct amination of alkyl halides or epoxides with ammonia, as well as the hydrogenation of nitriles or amides. However, these processes are usually costly due to the lack of organic raw materials with special functional groups and the tendency to generate massive waste.

The preferable route for synthesizing primary amines is the direct amination of alcohol compounds and the reductive amination of aldehydes and/or ketones. The process of direct amination of alcohol compounds involves the dehydrogenation of alcohols as a rate-determining step, usually requiring higher reaction temperature (160-250° C.). Although the reductive amination of aldehydes and/or ketones can be achieved under mild conditions (70-150° C.) by means of the catalysis of ammonia and hydrogen, the reaction substrate has a limited selection range and low availability. In addition, the synthesis of primary amines also faces the problems of high preparation cost and low selectivity of the catalyst, and difficulty of separating and recycling of the catalyst from the product, resulting in lacking of the potential for industrialization and affecting the process of industrialization.

Thus, it is urgent to provide a method for synthesizing primary amines with high yield, low cost and the potential for industrialization.

SUMMARY

In view of the foregoing, it is an objective of the present disclosure to provide a method for efficiently synthesizing primary amines.

On the basis of the objective described above, the present disclosure provides a method for efficiently synthesizing primary amines. The method comprises using carbonyl compounds or alcohol compounds as reaction substrate, liquid ammonia or alcohol solutions of ammonia as nitrogen source, and hydrogen as hydrogen source, and reacting in reaction medium catalyzed by a cobalt-based catalyst to obtain the primary amines.

It can be seen from the description above that the method for efficiently synthesizing primary amines provided by the present disclosure comprises using carbonyl compounds or alcohol compounds as reaction substrate, liquid ammonia or alcohol solutions of ammonia as nitrogen source, and hydrogen as hydrogen source, and reacting in reaction medium catalyzed by a cobalt-based catalyst to obtain the primary amines. Due to high catalytic activity, the method can realize the reductive amination of carbonyl compounds and the hydrogen-borrowing amination of alcohol compounds at low temperature in a short time to obtain the primary amine with high yield, and is applicable to a wide range of substrates. The obtained primary amines can be used as raw materials with high extra value for producing polymers, medicines, dyes and surfactants. Further, the cobalt-based catalyst has a good industrial application prospect because it is magnetic which can facilitate separation and recycling of the catalyst. Moreover, the inexpensive cobalt-based catalyst can significantly reduce industrialization cost.

BRIEF DESCRIPTION OF DRAWINGS

In order to more clearly describe the technical solutions in the present disclosure or in the related art, a brief introduction to the accompanying drawings required for the description of the examples or the related art will be provided below. Obviously, the accompanying drawings in the following description are merely the examples of the present disclosure. Those of ordinary skill in the art would also to derive other accompanying drawings from these accompanying drawings without making inventive efforts.

DETAILED DESCRIPTION OF THE EMBODIMENTS

Figure 1:
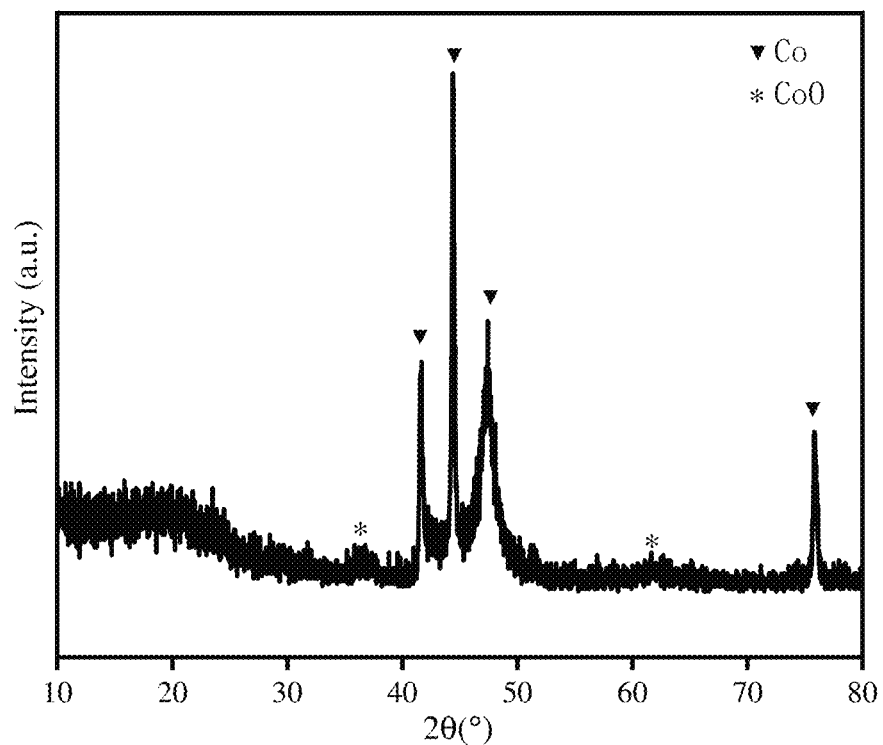
FIG. 1 is an x-ray diffraction (XRD) pattern of a core-shell Co@CoO catalyst provided in an example of the present disclosure.

In order to make the objective, the technical solutions and the advantages of the present disclosure clearer, the present disclosure will be described in further detail below with reference to the specific examples and the accompanying drawings.

It should be noted that, unless otherwise defined, the technical or scientific terms used in the examples of the present disclosure should have their ordinary meanings as understood by those of ordinary skill in the art to which the present disclosure pertains.

Nitrogen-containing compounds, especially primary amines, one of the most significant intermediates in chemical industry, is widely used in the synthesis of polymers, drugs, agricultural chemicals, dyes and surfactants. Currently, the general industrial route for the synthesis of primary amines is the direct amination of alkyl halides or epoxides with ammonia, as well as the hydrogenation of nitriles or amides. However, these processes are usually costly due to the lack of organic raw materials with special functional groups and the tendency to generate massive waste.

The preferable route for synthesizing primary amines is the direct amination of alcohol compounds and the reductive amination of aldehydes and/or ketones. The process of direct amination of alcohol compounds is not required to consume external hydrogen source in general and water is the main by-product, which is green and environment friendly. However, it involves the dehydrogenation of alcohols which is a rate-determining step, usually requiring higher reaction temperature (160-250° C.). Although the reductive amination of aldehydes and/or ketones can be achieved under mild conditions (70-150° C.) by means of the catalysis of ammonia and hydrogen, the reaction substrate has a limited selection range and low availability.

In addition, the synthesis of primary amines also faces the problems of high preparation cost and low selectivity of the catalyst, and difficulty of separating and recycling of the catalyst from the product, resulting in lacking of the potential for industrialization and affecting the process of industrialization. Consequently, it is urgent to develop an efficient catalytic system for continuously producing primary amines with high yield at low temperature in a short time, and it is also urgent to provide a method for synthesizing primary amines with high yield, low cost and the potential for industrialization.

In order to solve the problems described above, the present disclosure provides a method for efficiently synthesizing primary amines. The method comprises using carbonyl compounds or alcohol compounds as reaction substrate, liquid ammonia or alcohol solutions of ammonia as nitrogen source, and hydrogen as hydrogen source, and reacting in reaction medium catalyzed by a cobalt-based catalyst to obtain the primary amines.

In the present disclosure, the carbonyl compounds refer to the compounds structurally containing carbonyl group, and may be, for example, aldehyde carbonyl group-containing compounds or ketone carbonyl group-containing compounds, but not particularly limited. The alcohol compounds refer to the compounds structurally containing hydroxyl group, and may be, for example, saturated aliphatic hydrocarbon hydroxyl group-containing compounds, unsaturated aliphatic hydrocarbon hydroxyl group-containing compounds, or aromatic hydroxyl group-containing compounds, but not particularly limited. The alcohol solutions of ammonia refer to the solutions obtained by dissolving ammonia in alcohols, and may be, for example, the solutions obtained by dissolving ammonia in methanol, ethanol, propanol or isopropanol, but not particularly limited.

In some embodiments, the carbonyl compounds may comprise aliphatic aldehydes and/or ketones and aromatic aldehydes and/or ketones.

In the present disclosure, the aliphatic aldehydes and/or ketones may comprise aliphatic aldehydes and aliphatic ketones, wherein the aliphatic aldehydes refer to aldehyde compounds in which the carbonyl group is connected to an aliphatic hydrocarbon group and a hydrogen atom, and may comprise saturated aliphatic aldehydes and unsaturated aliphatic aldehydes. In the present disclosure, the number of carbon atoms contained in the aliphatic group, the substituents and specific structures of the aliphatic aldehydes are not limited. The aliphatic ketones refer to compounds in which the carbonyl group is connected to two aliphatic hydrocarbon groups, and may comprise saturated aliphatic ketones and unsaturated aliphatic ketones. In the present disclosure, the number of carbon atoms contained in the aliphatic hydrocarbon group, the substituents and specific structures of the aliphatic ketones are not limited. Preferably, the aliphatic aldehydes and/or ketones may comprise at least one of acetone, propionaldehyde, butanone, butyraldehyde, 2-pentanone, valeraldehyde, 4-heptanone, octanal, 2-octanone, and 5-nonanone.

The aromatic aldehydes and/or ketones may comprise aromatic aldehydes and aromatic ketones, wherein the aromatic aldehydes refer to aldehyde compounds in which the carbonyl group is connected to an aromatic hydrocarbon group and a hydrogen atom. In the present disclosure, the number of carbon atoms contained in the aromatic hydrocarbon group, the substituents and specific structures of the aromatic aldehydes are not limited. The aromatic ketones may comprise pure aromatic ketones and mixed aromatic ketones, wherein the pure aromatic ketones refer to compounds in which carbonyl group is connected to two aromatic hydrocarbon groups, and the mixed aromatic ketones refer to compounds in which the carbonyl group is connected to an aromatic hydrocarbon group and a non-aromatic hydrocarbon group. In the present disclosure, the number of carbon atoms contained in the aromatic hydrocarbon group and the non-aromatic hydrocarbon group, the substituents and particular structures of the aromatic ketones are not limited. Preferably, the aromatic aldehydes and/or ketones may comprise at least one of benzaldehyde, phenylacetaldehyde, phenylpropionaldehyde, acetophenone, 4-chloroacetophenone, 2-bromoacetophenone, 2-methoxypropiophenone, 2-naphthaldehyde, 4-hydroxyphenyl acetophenone, 4-methoxybenzaldehyde, and benzophenone.

In some embodiments, the alcohol compounds may comprise aliphatic alcohols and aromatic alcohols.

In the present disclosure, the aliphatic alcohols refer to alcohol compounds in which the hydroxyl group is connected to an aliphatic hydrocarbon group, and may comprise saturated aliphatic alcohols and unsaturated aliphatic alcohols. In the present disclosure, the number of carbon atoms contained in the aliphatic hydrocarbon group, the substituents and specific structures of the aliphatic alcohols are not particularly limited. The aromatic alcohols refer to compounds in which the hydroxyl group is connected to a carbon atom on branched chain of a benzene ring in an aromatic hydrocarbon group. In the present disclosure, the number of carbon atoms contained in the aromatic hydrocarbon group, the substituents and specific structures of the aromatic alcohols are not limited. Preferably, the alcohol compounds may comprise at least one of propanol, n-butanol, cyclopentanol, cyclohexanol, 1-octanol, and benzyl alcohol.

In some embodiments, the alcohol solutions of ammonia may comprise at least one of methanol solution of ammonia (ammonia/methanol), ethanol solution of ammonia (ammonia/ethanol) and isopropanol solution of ammonia (ammonia/isopropanol).

In some embodiments, the reaction medium may comprise organic solvents, wherein the organic solvents may comprise at least one of methanol, ethanol, isopropanol, ethylene glycol dimethyl ether, tetrahydrofuran, toluene, and p-xylene, and preferably, the reaction medium is selected from methanol and p-xylene.

In some embodiments, a mass ratio of the reaction substrate to the cobalt-based catalyst is 1:(0.01-2).

In the present disclosure, the reaction substrate comprises carbonyl compounds and alcohol compounds. The "mass ratio of the reaction substrate to the cobalt-based catalyst" refers to a ratio of mass of the reaction substrate to mass of the cobalt-based catalyst, wherein the ratio may be 1:(0.01-2), for example, 1:0.01, 1:0.1, 1:0.5, 1:1, 1:1.5, or 1:2, but not particularly limited.

In some embodiments, a mass ratio of the reaction substrate to the reaction medium may be 1:(1-60), preferably 1:(1-30).

In the present disclosure, the "mass ratio of the reaction substrate to the reaction medium" refers to a ratio of mass of the reaction substrate to mass of the reaction medium, wherein the ratio may be 1:(1-60), preferably 1:(1-30), for example, 1:5, 1:10, 1:15, 1:20, or 1:25, which is not particularly limited.

In some embodiments, a concentration of the alcohol solutions of ammonia may be 2 M-7 M.

In the present disclosure, the concentration of the alcohol solutions of ammonia refers to a molar concentration of ammonia in alcohols, wherein the molar concentration may be 2 M-7 M, for example, 2 M, 3 M, 4 M, 5 M, 6 M, or 7 M, but not particularly limited.

In some embodiments, a pressure of the gasified liquid ammonia is 0.1-1 MPa, preferably 0.3-0.8 MPa.

In the present disclosure, the pressure of the gasified liquid ammonia refers to a pressure after liquid ammonia being gasified into ammonia gas, and may be 0.1-1 MPa, preferably 0.3-0.8 MPa, for example, 0.1 MPa, 0.3 MPa, 0.5 MPa, 0.8 MPa, or 1 Mpa, but not particularly limited.

In some embodiments, a pressure of the hydrogen may be 0.5-5 MPa, preferably 0.5-2 MPa.

In some embodiments, the reaction temperature may be 70-200° C., preferably 70-150° C.

In the present disclosure, the reaction temperature refers to a temperature required to generate the primary amine from the reaction substrate, and may be 70-200° C., preferably 70-150° C., for example, 70° C., 100° C., 130° C., 150° C., 170° C., or 200° C., but not particularly limited. The cobalt-based catalyst provided by the present disclosure has high catalytic activity, and can catalyze the reductive amination of carbonyl compounds and the hydrogen-borrowing amination of ketone compounds at low temperatures, thereby conserving energy and improving synthesis efficiency.

In some embodiments, the reaction time may be 0.5-25 h, preferably 2-24 h.

In the present disclosure, the reaction time refers to the time required to generate the primary amine from the reaction substrate, and may be 0.5-25 h, preferably 2-24 h, for example, 0.5 h, 2 h, 5 h, 10 h, 15 h, 20 h, 24 h, or 25 h, but not particularly limited. The cobalt-based catalyst provided by the present disclosure has high catalytic activity, and can catalyze the reductive amination of carbonyl compounds and the hydrogen-borrowing amination of ketone compounds in a short time, thereby shortening the reaction time and improving synthesis efficiency.

In some embodiments, the primary amines may be synthesized by a batch reaction process or a continuous reaction process, wherein the reactors used in the batch reaction process may comprise batch reactors, fluidized beds and slurry beds, and the reactors used in the continuous reaction process may comprise fixed beds and movable beds.

A process for preparing primary amines in batch reactors by using carbonyl compounds as reaction substrate provided in the present disclosure may comprise the steps of preparing a prescription amount of carbonyl compound, cobalt-based catalyst and reaction medium, adding the carbonyl compound, the cobalt-based catalyst and the reaction medium into a batch reactor, and reacting for 0.5-5 h at the partial pressure of ammonia of 0.3-0.8 MPa, the pressure of hydrogen of 1-4 MPa and the reaction temperature of 70-150° C.

A process for preparing primary amines in batch reactors by using alcohol compounds as reaction substrate provided in the present disclosure may comprise the steps of preparing a prescription amount of an alcohol compound, a cobalt-based catalyst and a reaction medium, adding the alcohol compound, the cobalt-based catalyst and the reaction medium into a batch reactor, and reacting for 15-25 h at the partial pressure of ammonia of 0.3-0.8 MPa, the pressure of hydrogen of 0.2-0.8 MPa, and the reaction temperature of 160-200° C.

The present disclosure further provides a method for determining the conversion and the yield when synthesizing primary amines. The determination method may comprise the steps of qualitative analysis of the reaction product by gas chromatography-mass spectrometry (GC-MS Agilent 7890A-5975C) and quantitative analysis of the reaction product by gas chromatography (GC Agilent 7890A) by using chromatographic column HP-5, wherein programmed temperature conditions comprise: maintained at 50° C. for 10 mins, increased to 250° C. at rate of 10° C./min, and maintained at 250° C. for 5 mins.

In some embodiments, the cobalt-based catalyst comprises a core-shell Co@CoO catalyst, wherein the core is cobalt and the shell is cobalt monoxide (CoO) containing oxygen vacancies, respectively.

FIG. 1 is an x-ray diffraction (XRD) pattern of a core-shell Co@CoO catalyst provided in the present disclosure, wherein crystal phase information of the core-shell Co@CoO catalyst is obtained through XRD. A diffraction peak of metal Co can be clearly distinguished in the figure, and a diffraction peak of CoO can be also found in FIG. 1, indicating that the core-shell Co@CoO catalyst prepared in the present disclosure contains both a metal Co phase and a CoO phase.

Figure 2:
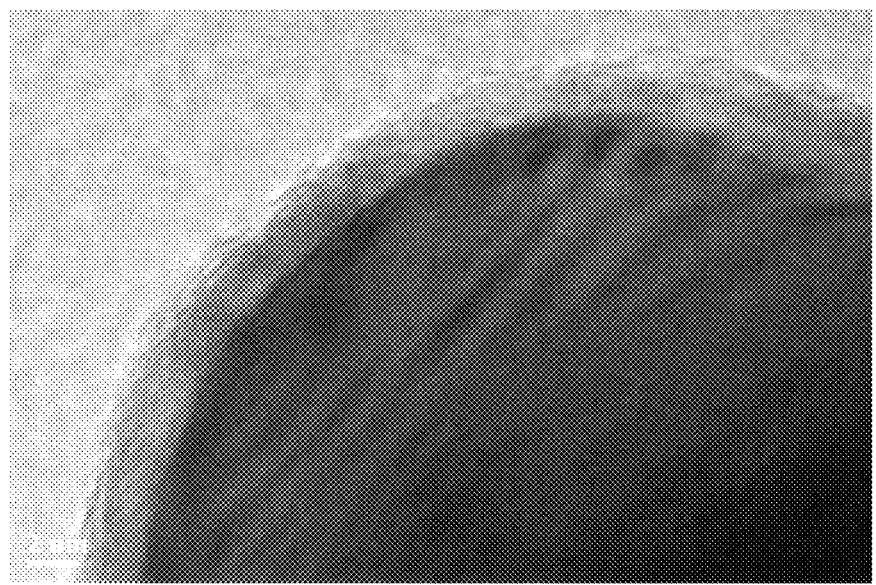
FIG. 2 is a transmission electron microscope (TEM) image of an active phase of the core-shell Co@CoO catalyst provided in the example of the present disclosure.

FIG. 2 is a transmission electron microscope (TEM) image of an active phase of the core-shell Co@CoO catalyst provided in the present disclosure, wherein morphology information of the core-shell Co@CoO catalyst is obtained through TEM. A core-shell structure of the core-shell Co@CoO catalyst can be clearly seen in the figure, and a measurement shows that the outer layer is crystal lattice stripes of CoO, and the inner layer is crystal lattice stripes of metal Co, indicating that the core-shell Co@CoO catalyst prepared in the present disclosure has the core-shell structure with the outer layer of CoO and the inner layer of Co.

In the present disclosure, the active phase of the core-shell Co@CoO catalyst is CoO. The study found that the by-products of amination reaction are mainly diamine compounds generated by hydrogenation of Schiff alkali as an intermediate product and coupling compounds generated by aldol condensation of the substrate. Generally, during the process of generating the by-products, the hydrogenation catalytic active center of Schiff alkali is metal center, hydrogen is dissociated by the metal center, and then the hydrogenation reaction is carried out. The products of aldol condensation of the substrate are mainly carried out at the acid center. In the amination process, since the primary amine generated at first has a nucleophilic property far greater than ammonia, it is inevitable to generate Schiff alkali, and a conventional supported catalyst cannot inhibit the Schiff alkali from being hydrogenated, resulting in poor reaction selectivity. In addition, in the presence of ammonia, the active center on a surface of the catalyst is prone to be covered, resulting in poor reaction activity. A rate-determining step of hydrogen-borrowing amination of alcohol compounds is the first step of dehydrogenation process, and the presence of ammonia affects the dehydrogenation rate to a great extent.

In the present disclosure, a cobalt monoxide active site containing abundant oxygen vacancies is introduced into the cobalt-based catalyst. Hydrogen can be dissociated on the surface of cobalt monoxide, resulting in high hydrogenation activity. In addition, cobalt monoxide on the surface can effectively inhibit the hydrogenation of Schiff alkali as the intermediate product. The surface of the cobalt-based catalyst has less acid sites, which can inhibit aldol condensation side reaction of carbonyl compounds, and improve the selectivity of primary amines as target product. The cobalt monoxide on the surface of the cobalt-based catalyst in the present disclosure has a certain of dehydrogenation capacity, and can still dehydrogenate alcohol compounds in the presence of ammonia and carry out a subsequent amination reaction, and the cobalt monoxide on the surface can also inhibit the hydrogenation of Schiff alkali as the intermediate product and improve the yield of the primary amines.

In some embodiments, a method for preparing the core-shell Co@CoO catalyst comprises the steps of preparing a precipitate from cobalt source and precipitatant by precipitation method, and then optionally calcining the precipitate to obtain the precursor, and finally optionally reducing the precursor in a reducing gas to obtain the core-shell Co@CoO catalyst.

The precipitation method in the present disclosure has the conventional meaning in the art, and may be carried out according to any conventional precipitation method in the art, as long as the cobalt source and the precipitatant can be co-precipitated to obtain the precipitate, which will not be described in detail herein.

Preferably, the cobalt source is used in an amount such that a content of an active component in the prepared core-shell Co@CoO catalyst meets a corresponding content requirement.

Preferably, the present disclosure does not limit a specific kind of the cobalt source, as long as the core-shell Co@CoO catalyst can be prepared through the method described above. More preferably, the cobalt source may comprise at least one of salts, esters and complexes containing Co element, wherein the salts may comprise at least one of nitrate, acetate and chlorine salt, and the complexes may be any existing complex containing Co element, which will not be described in detail herein. Further preferably, the cobalt source may be selected from at least one of cobalt nitrate, cobalt acetate, cobalt carbonyl and cobalt chloride.

Preferably, the present disclosure does not limit a specific kind of the precipitatant, as long as it can be co-precipitated with the cobalt source. More preferably, the precipitatant may comprise at least one of amides, alkalis and salts capable of being co-precipitated with the cobalt source. Further preferably, the precipitatant may be selected from at least one of sodium hydroxide, sodium carbonate, sodium bicarbonate, ammonium carbonate, ammonium bicarbonate and urea.

Preferably, a calcination temperature may be 400-450° C., for example, 400° C., 420° C., or 450° C., but not particularly limited.

Preferably, a volume fraction of hydrogen in reducing gas may be 5-30%, preferably 5-15%.

In the present disclosure, the reducing gas refers to gas for reducing the precursor, and is mixed gas of hydrogen and argon. The volume fraction of hydrogen refers to a volume percentage of hydrogen in the mixed gas, which may be 5-30%, preferably 5-15%, for example, 5%, 10%, 15%, 20%, 25%, or 30%, and is not particularly limited.

Preferably, a flow rate of the reducing gas may be 10-100 ml/min, more preferably 10-40 ml/min, for example, 10 ml/min, 30 ml/min, 40 ml/min, 60 ml/min, 80 ml/min, or 100 ml/min, but not particularly limited.

Preferably, a reduction temperature may be 100-400° C., more preferably 200-350° C.

In the present disclosure, the reaction temperature refers to a temperature for reducing the precursor in the reducing gas, and may be 100-400° C., preferably 200-350° C., for example, 100° C., 200° C., 225° C., 250° C., 275° C., 300° C., 350° C., or 400° C., but not particularly limited.

Preferably, a reduction time may be 1-6 h, more preferably 1-3 h.

In the present disclosure, the reaction time refers to a time for reducing the precursor in the reducing gas, and may be 1-6 h, preferably 1-3 h, for example, 1 h, 2 h, 3 h, 4 h, 5 h, or 6 h, but not particularly limited.

A method for preparing a core-shell Co@CoO catalyst through a precipitation method provided by the present disclosure may comprise: a cobalt source and a precipitator being co-precipitated through the precipitation method to obtain a precipitate, the precipitate being calcined at 400-450° C. to obtain a precursor, and the precursor being reduced for 1-6 h in reducing gas at a flow rate of 10-100 ml/min and a volume fraction of hydrogen of 5-30% to prepare the core-shell Co@CoO catalyst.

In some embodiments, a method for preparing the core-shell Co@CoO catalyst may comprise preparing the precursor by a high-temperature thermal decomposition method, and then optionally reducing the precursor to obtain the core-shell Co@CoO catalyst.

In the present disclosure, the high-temperature thermal decomposition method has the conventional meaning in the art, and may be carried out according to any conventional high-temperature thermal decomposition method in the art, as long as the precursor can be prepared, which will not be described in detail herein.

Preferably, the cobalt source is used in an amount such that a content of an active component in the prepared core-shell Co@CoO catalyst meets a corresponding content requirement.

Preferably, the present disclosure does not limit a specific kind of the cobalt source, as long as the core-shell Co@CoO catalyst can be prepared through the method described above. More preferably, the cobalt source may comprise at least one of salts, esters and complexes containing Co element, wherein the salts may comprise at least one of nitrate, acetate and chlorine salt, and the complexes may be any existing complex containing Co element, which will not be described in detail herein. Further preferably, the cobalt source may be selected from at least one of cobalt nitrate and cobalt acetate.

Preferably, conditions of the high-temperature thermal decomposition method comprise: a calcination temperature of 300-600° C., more preferably, 400-550° C., for example, 300° C., 350° C., 400° C., 450° C., 500° C., 550° C., or 600° C., but not particularly limited.

Preferably, a volume fraction of hydrogen in the reducing gas may be 5-30%, more preferably 5-15%, for example, 5%, 8%, 10%, 12%, 15%, 20%, 25%, or 30%, but not particularly limited.

Preferably, a flow rate of the reducing gas may be 10-100 ml/min, more preferably 10-40 ml/min, for example, 10 ml/min, 30 ml/min, 40 ml/min, 50 ml/min, 60 ml/min, 80 ml/min, or 100 ml/min, but not particularly limited.

Preferably, a reduction temperature may be 100-400° C., more preferably, 200-350° C., for example, 100° C., 150° C., 200° C., 225° C., 250° C., 275° C., 300° C., 350° C., 375° C., or 400° C., but not particularly limited.

Preferably, a reaction time may be 1-6 h, more preferably 1-3 h, for example, 1 h, 2 h, 3 h, 4 h, 5 h, or 6 h, but not particularly limited.

A method for preparing a core-shell Co@CoO catalyst through a high-temperature thermal decomposition method provided by the present disclosure may comprise: calcining a cobalt source at 300-600° C. to obtain a precursor, and reducing the precursor for 1-6 h in a reducing gas at a flow rate of 10-100 ml/min and a volume fraction of hydrogen of 5-30%, to prepare the core-shell Co@CoO catalyst.

In some embodiments, the cobalt-based catalyst may comprise a supported cobalt-based catalyst. The present disclosure does not limit a specific kind of a carrier, as long as the cobalt source can be supported. Preferably, the carrier of the supported cobalt-based catalyst may comprise at least one of metal oxides, $SiO_2$, and activated carbon.

The present disclosure does not limit a specific kind of the metal oxides, as long as the cobalt source can be supported. Preferably, the metal oxides may comprise at least one of IIIA-group metal oxides, IIA-group metal oxides, IVB-group metal oxides, lanthanide metal oxides and VIB-group metal oxides, and more preferably, the metal oxides can be selected from at least one of $Al_2O_3$, MgO, $MgAl_2O_4$, $TiO_2$, $ZrO_2$, $CeO_2$, and $MoO_3$.

In some embodiments, a method for preparing the supported cobalt-based catalyst may comprise a cobalt source and a carrier precursor being co-precipitated to prepare a precipitate, and then the precipitate being optionally calcined to obtain the precursor, and finally the precursor being optionally reduced in a reducing gas to obtain the supported cobalt-based catalyst.

In the present disclosure, the co-precipitation has the conventional meaning in the art, and may be carried out according to any existing co-precipitation method in the art, as long as the cobalt source can be introduced into the carrier, which will not be described in detail herein.

Preferably, the cobalt source is used in an amount such that a content of an active component in the prepared supported cobalt-based catalyst meets a corresponding content requirement.

The present disclosure does not limit a specific kind of the cobalt source, as long as the supported cobalt-based catalyst can be prepared through the method described above. Preferably, the cobalt source may comprise at least one of salts, esters and complexes containing Co element, wherein the salts may comprise at least one of nitrate, acetate and a chlorine salt, and the complexes may be any existing complex containing Co element, which will not be described in detail herein. More preferably, the cobalt source may be selected from cobalt chloride.

Preferably, the carrier precursor comprises at least one of IIIA-group metal salts, IIA-group metal salts, IVB-group metal salts, lanthanide metal salts, and VIB-group metal salts.

The present disclosure does not limit a specific kind of the carrier precursor, as long as the carrier can be prepared to support the cobalt source. Preferably, the carrier precursor may comprise at least one of IIIA-group metal salts, IIA-group metal salts, IVB-group metal salts, lanthanide metal salts, and VIB-group metal salts, wherein the salts may be at least one of nitrate, phosphate, sulfate, carbonate, etc. More preferably, the carrier precursor is selected from magnesium nitrate, aluminum nitrate or cerium nitrate.

Preferably, a calcination temperature may be 350-450° C., for example, 350° C., 380° C., 400° C., 420° C., or 450° C., but not particularly limited.

Preferably, a volume fraction of hydrogen in the reducing gas may be 5-30%, preferably 5-15%, for example, 5%, 10%, 15%, 20%, 25%, or 30%, but not particularly limited.

Preferably, a flow rate of the reducing gas may be 10-100 ml/min, preferably 10-40 ml/min, for example, 10 ml/min, 20 ml/min, 40 ml/min, 60 ml/min, or 80 ml/min, but not particularly limited.

Preferably, a reduction temperature may be 100-400° C., preferably, 200-350° C., for example, 100° C., 200° C., 250° C., 275° C., 300° C., 350° C., or 400° C., but not particularly limited.

Preferably, a reaction time may be 1-6 h, preferably 1-3 h, for example, 1 h, 2 h, 3 h, 4 h, 5 h, or 6 h, but not particularly limited.

In some embodiments, a method for preparing the supported cobalt-based catalyst may comprise preparing a carrier, and then supporting a cobalt source on the carrier through an incipient-wetness impregnation method, a wet impregnation method, or a precipitation deposition method, and optionally being calcined to prepare a precursor, and finally optionally reducing the precursor to obtain the supported cobalt-based catalyst.

In the present disclosure, the incipient-wetness impregnation method, the wet impregnation method and the precipitation deposition method have the conventional meanings in the art, and may be carried out according to any existing incipient-wetness impregnation method, wet impregnation method or precipitation deposition method in the art, as long as the cobalt source and the carrier can be impregnated, which will not be described in detail herein.

Preferably, the cobalt source is used in an amount such that a content of an active component in the prepared supported cobalt-based catalyst meets a corresponding content requirement.

The present disclosure does not limit a specific kind of the cobalt source, as long as the supported cobalt-based catalyst can be prepared through the method described above. Preferably, the cobalt source may comprise at least one of salts, esters, and complexes containing Co element. More preferably, the cobalt source may be selected from cobalt chloride.

Preferably, a calcination temperature may be 350-450° C., for example, 350° C., 380° C., 400° C., 410° C., 420° C., or 450° C., but not particularly limited.

Preferably, a volume fraction of hydrogen in the reducing gas may be 5-30%, preferably 5-15%, for example, 5%, 10%, 15%, 20%, 27%, or 30%, but not particularly limited.

Preferably, a flow rate of the reducing gas may be 10-100 ml/min, preferably 10-40 ml/min, for example, 10 ml/min, 20 ml/min, 30 ml/min, 40 ml/min, 60 ml/min, or 100 ml/min, but not particularly limited.

Preferably, a reduction temperature may be 100-400° C., preferably, 200-350° C., for example, 100° C., 200° C., 225° C., 250° C., 275° C., 300° C., 350° C., or 400° C., but not particularly limited.

Preferably, a reaction time may be 1-6 h, preferably 1-3 h, for example, 1 h, 2 h, 3 h, 4 h, 5 h, or 6 h, but not particularly limited.

Due to high catalytic activity, the method for efficiently synthesizing primary amines provided by the present disclosure can realize the reductive amination of carbonyl compounds and the hydrogen-borrowing amination of alcohol compounds at low temperatures in a short time to obtain the primary amines with high yield, and is applicable to a wide range of substrates. The obtained primary amines can be used as raw materials with high extra value for producing polymers, medicines, dyes and surfactants. Further, the cobalt-based catalyst has a good industrial application prospect because it is magnetic which can facilitate separation and recycling of the catalyst. Moreover, the inexpensive cobalt-based catalyst can significantly reduce industrialization cost.

The following will describe the present disclosure in detail in conjunction with the examples.

In the following examples, the process for preparing primary amines by reductive amination catalyzed by cobalt-based catalyst in a batch reactor by using aldehyde and/or ketone compounds as reaction substrate comprises: adding 0.18 g of reaction substrate, 0.02 g of cobalt-based catalyst, and 5 mL of reaction medium into a 50 mL batch reactor, and reacting for 0.5-5 h at ammonia partial pressure of 0.3-0.8 MPa, hydrogen partial pressure of 1-4 MPa, and a temperature of 70° C.-150° C. The reaction products were qualitatively analyzed through gas chromatography-mass spectrometry (GC-MS Agilent 7890A-5975C) and quantitatively analyzed through gas chromatography (GC Agilent 7890A) by using chromatographic column HP-5, wherein programmed temperature conditions comprise: maintained at 50° C. for 10 mins, increased to 250° C. at rate of 10° C./min, and maintained at 250° C. for 5 mins.

In the following examples, the process for preparing primary amines by hydrogen-borrowing amination catalyzed by cobalt-based catalyst in a batch reactor by using alcohol compounds as reaction substrate comprises: adding 0.18 g of reaction substrate, 0.04 g of catalyst, and 5 mL of reaction medium into a 50 mL batch reactor, and reacting for 15-25 h at ammonia partial pressure of 0.3-0.8 MPa, hydrogen partial pressure of 0.2-0.8 MPa and a temperature of 160° C.-200° C. The reaction products were qualitatively analyzed through gas chromatography-mass spectrometry (GC-MS Agilent 7890A-5975C) and quantitatively analyzed through gas chromatography (GC Agilent 7890A) by using chromatographic column HP-5, wherein the programmed temperature conditions comprise: maintained at 50° C. for 10 mins, increased to 250° C. at rate of 10° C./min and maintained at 250° C. for 5 mins.

In the following examples, the process of preparing a core-shell Co@CoO catalyst by a precipitation method comprises: dissolving 60 mmol of cobalt source into 200 ml of deionized water to serve as solution A; and dissolving 69 mmol of precipitatant into 200 ml of deionized water to serve as solution B. The solution B was slowly dripped into the solution A while stirring vigorously in a water bath at 65° C., and the solution B was dripped until pH of the mixed solution was 9. The mixed solution was stirred continuously in the water bath at 65° C. for 1 h, and then left to stand at room temperature for 12 h. The mixed solution was filtered, washed with deionized water several times, placed into an oven of 100° C. to be dried over night, then ground, and calcined in a muffle furnace at 450° C. for 4 h to obtain $Co_3O_4$ as a precursor; and then the precursor $Co_3O_4$ was reduced for 1-3 h in reducing gas with a volume fraction of $H_2$ of 5-10% and a flow rate of 10-40 ml/min at a temperature of 225-400° C., to prepare the core-shell Co@CoO catalyst.

Examples 1-7

In Examples 1-7, the core-shell Co@CoO catalyst is prepared by precipitation method, wherein cobalt nitrate serves as the cobalt source, sodium carbonate serves as the precipitant, the calcination temperature is 450° C., and the reduction temperature is 300° C. Examples 1-7 differ from one other in volume fractions of hydrogen in the reducing gas, flow rates of the reducing gas, and reduction times.

In Examples 1-7, the primary amine is prepared by catalysis of the cobalt-based catalyst, wherein 0.18 g of cyclopentanone serves as the reaction substrate, 0.02 g of the core-shell Co@CoO catalyst serves as the catalyst, 5 ml of methanol serves as the reaction medium, the partial pressure of ammonia is 0.3 MPa, the partial pressure of hydrogen is 2 MPa, the reaction temperature is 90° C., the reaction time is 4 h, and the batch reactor is used to obtain cyclopentylamine as the reaction product. The conversion of the reaction substrate and the yield of the reaction product in each example are measured, and results are shown in Table 1.

TABLE 1

| | Volume fraction of $H_2$ (%) | Gas flow rate (ml/min) | Reduction time (h) | Conversion of cyclopentanone (%) | Yield of cyclopentylamine (%) |
|---|---|---|---|---|---|
| Example 1 | 5 | 30 | 2 | 92 | 70 |
| Example 2 | 10 | 30 | 2 | 100 | 97.2 |
| Example 3 | 15 | 30 | 2 | 100 | 96.7 |
| Example 4 | 10 | 10 | 2 | 100 | 79 |
| Example 5 | 10 | 40 | 2 | 100 | 90 |
| Example 6 | 10 | 30 | 1 | 81 | 50 |
| Example 7 | 10 | 30 | 3 | 100 | 95 |

Examples 8-13

In Examples 8-13, the core-shell Co@CoO catalyst is prepared by precipitation method, wherein cobalt nitrate serves as the cobalt source, sodium carbonate serves as the precipitant, the calcination temperature is 450° C., the volume fraction of hydrogen in reducing gas is 10%, the flow rate of reducing gas is 30 ml/min, and the reduction time is 2 h. Examples 8-13 differ from one another in the reduction temperatures, and particularly the reduction temperatures in Examples 8-13 are 225° C., 250° C., 275° C., 300° C., 350° C. and 400° C., separately, and the obtained core-shell Co@CoO catalysts are Co@CoO-P-225, Co@CoO-P-250, Co@CoO-P-275, Co@CoO-P-300, Co@CoO-P-350 and Co@CoO-P-400, separately.

In Examples 8-13, the primary amine is prepared by catalysis of the cobalt-based catalyst, wherein 0.18 g of cyclopentanone serves as the reaction substrate, 0.02 g of the core-shell Co@CoO catalyst serves as the catalyst, 5 ml of methanol serves as the reaction medium, the partial pressure of ammonia is 0.3 MPa, the partial pressure of hydrogen is 2 MPa, the reaction temperature is 90° C., the reaction time is 4 h, and the batch reactor is used to obtain cyclopentylamine as the reaction product. The conversion of the reaction substrate and the yield of the reaction product in each example are measured, and results are shown in Table 2.

TABLE 2

| | Catalyst | Conversion of cyclopentanone (%) | Yield of cyclopentylamine (%) |
|---|---|---|---|
| Example 8 | Co@CoO-P-225 | 42.2 | 22.0 |
| Example 9 | Co@CoO-P-250 | 88 | 80.0 |
| Example 10 | Co@CoO-P-275 | 100 | 88.5 |
| Example 11 | Co@CoO-P-300 | 100 | 97.2 |
| Example 12 | Co@CoO-P-350 | 100 | 60.0 |
| Example 13 | Co@CoO-P-400 | 100 | 45.0 |

* P denotes a cobalt-based catalyst prepared through a precipitation method.

Examples 14-18

In Examples 14-18, the core-shell Co@CoO catalyst is prepared by high-temperature thermal decomposition method, wherein 5 g of cobalt nitrate as the cobalt source is subjected to high-temperature calcination in a muffle furnace at 500° C. for 5 h to obtain $Co_3O_4$ as the precursor. In Examples 14-18, the precursor of $Co_3O_4$ is reduced, the volume fraction of hydrogen in the reducing gas is 10%, the flow rate of the reducing gas is 30 ml/min, and the reduction time is 2 h. Examples 14-18 differ from one another in the reduction temperatures, and particularly, the reduction temperatures in Examples 14-18 are 225° C., 250° C., 275° C., 300° C., 350° C. and 400° C., separately, and the obtained core-shell Co@CoO catalysts are Co@CoO-P-225, Co@CoO-P-250, Co@CoO-P-275, Co@CoO-P-300, Co@CoO-P-350 and Co@CoO-P-400, separately.

In Examples 14-18, the primary amine are prepared by catalysis of the cobalt-based catalyst, wherein 0.18 g of cyclopentanone serves as the reaction substrate, 0.02 g of the core-shell Co@CoO catalyst serves as the catalyst, 5 ml of methanol serves as the reaction medium, the partial pressure of ammonia is 0.3 MPa, the partial pressure of hydrogen is 2 MPa, the reaction temperature is 90° C., the reaction time is 4 h, and the batch reactor is used to obtain cyclopentylamine as the reaction product. The conversion of the reaction substrate and the yield of the reaction product in each example are measured, and results are shown in Table 3.

TABLE 3

| Catalyst | Conversion of cyclopentanone (%) | Yield of cyclopentylamine (%) |
| --- | --- | --- |
| Example 14 | Co@CoO-D-250 | 100 | 25.3 |
| Example 15 | Co@CoO-D-275 | 100 | 50.5 |
| Example 16 | Co@CoO-D-300 | 100 | 45.1 |
| Example 17 | Co@CoO-D-350 | 100 | 30.2 |
| Example 18 | Co@CoO-D-400 | 100 | 35.6 |

* D denotes the cobalt-based catalyst prepared by high-temperature thermal decomposition method.

The results in Table 3 show that all the cobalt-based catalysts prepared by the high-temperature thermal decomposition method have high catalytic activity.

Examples 19-21

In Examples 19-21, the core-shell Co@CoO catalyst is prepared by precipitation method, wherein sodium carbonate serves as precipitant, the calcination temperature is 450° C., the reduction temperature is 300° C., the volume fraction of hydrogen in the reducing gas is 10%, the flow rate of the reducing gas is 30 ml/min, and the reduction time is 2 h. Examples 19-21 differ from one another in the cobalt sources, and particularly, the cobalt sources used in Examples 19-21 are cobalt acetate, cobalt chloride and cobalt carbonyl, separately.

In Examples 19-21, the primary amine is prepared by catalysis of the cobalt-based catalyst, wherein 0.18 g of cyclopentanone serves as the reaction substrate, 0.02 g of the core-shell Co@CoO catalyst serves as the catalyst, 5 ml of methanol serves as the reaction medium, the partial pressure of ammonia is 0.3 MPa, the partial pressure of hydrogen is 2 MPa, the reaction temperature is 90° C., the reaction time is 4 h, and the batch reactor is used to obtain cyclopentylamine as the reaction product. The conversion of the reaction substrate and the yield of the reaction product in each example are measured, and results are shown in Table 4.

TABLE 4

| | Cobalt source | Catalyst | Conversion of cyclopentanone (%) | Yield of cyclopentylamine (%) |
| --- | --- | --- | --- | --- |
| Example 19 | Cobalt acetate | Co@CoO-P-300 | 85 | 65 |
| Example 20 | Cobalt chloride | Co@CoO-P-300 | 71 | 30 |
| Example 21 | Cobalt carbonyl | Co@CoO-P-300 | 64 | 43 |

The results in Table 4 show that the cobalt-based catalysts prepared from various cobalt sources all have high catalytic activity.

Examples 22-26

In Examples 22-26, the core-shell Co@CoO catalyst is prepared by precipitation method, wherein cobalt nitrate serves as a cobalt source, the calcination temperature is 450° C., the reduction temperature is 300° C., the volume fraction of hydrogen in the reducing gas is 10%, the flow rate of the reducing gas is 30 ml/min, and the reduction time is 2 h. Examples 22-26 differ from one another in the precipitants, and particularly, the precipitants used in Examples 22-26 are sodium hydroxide, sodium bicarbonate, ammonium carbonate, ammonium bicarbonate and urea, separately.

In Examples 22-26, the primary amine is prepared by catalysis of the cobalt-based catalyst, wherein 0.18 g of cyclopentanone serves as the reaction substrate, 0.02 g of the core-shell Co@CoO catalyst serves as the catalyst, 5 ml of methanol serves as the reaction medium, the partial pressure of ammonia is 0.3 MPa, the partial pressure of hydrogen is 2 MPa, the reaction temperature is 90° C., the reaction time is 4 h, and the batch reactor is used to obtain cyclopentylamine as the reaction product. The conversion of the reaction substrate and the yield of the reaction product in each example are measured, and results are shown in Table 5.

TABLE 5

| | Precipitator | Catalyst | conversion of cyclopentanone (%) | Yield of cyclopentylamine (%) |
| --- | --- | --- | --- | --- |
| Example 22 | Sodium hydroxide | Co@CoO-P-300 | 80 | 21 |
| Example 23 | Sodium bicarbonate | Co@CoO-P-300 | 90 | 45 |
| Example 24 | Ammonium carbonate | Co@CoO-P-300 | 91 | 81 |
| Example 25 | Ammonium bicarbonate | Co@CoO-P-300 | 96 | 56 |
| Example 26 | Urea | Co@CoO-P-300 | 94 | 62 |

The results in Table 5 show that the cobalt-based catalysts prepared from various precipitants all have high catalytic activity.

Examples 27-35

In Examples 27-35, the supported cobalt-based catalyst is prepared by impregnating the carrier with cobalt chloride solution at the loading amount of 10% through the incipient-wetness impregnation method, wherein the loading amount of 10% means that a mass percentage of cobalt in the total amount of the supported cobalt-based catalyst is 10%. After drying in an oven of 100° C. for 12 h, the catalyst precursor is placed in a nitrogen atmosphere for high-temperature treatment, wherein particularly 1 g of the precursor is heated to 450° C. from room temperature in a quartz tube in 2 h, maintained for 4 h, and automatically cooled; and then the cooled catalyst is reduced in $H_2$/Ar atmosphere at the volume fraction of $H_2$ of 10%, more particularly, 1 g of the precursor is heated to 250° C. from room temperature in a quartz tube in 1 h and maintained for 2 h with the gas flow rate of 60 ml/min. Example 27-35 differ from one another in the carriers, and particularly, the carriers used in Example 27-35 are $Al_2O_3$, MgO, $MgAl_2O_4$, $TiO_2$, $ZrO_2$, $CeO_2$, $MoO_3$, $SiO_2$, and activated carbon, separately.

In Examples 27-35, the primary amine is prepared by catalysis of the cobalt-based catalyst, wherein 0.18 g of cyclopentanone serves as the reaction substrate, 0.02 g of the supported cobalt-based catalyst serves as the catalyst, 5 ml of methanol serves as the reaction medium, the partial pressure of ammonia is 0.3 MPa, the partial pressure of hydrogen is 2 MPa, the reaction temperature is 90° C., the reaction time is 4 h, and the batch reactor is used to obtain cyclopentylamine as the reaction product. The conversion of the reaction substrate and the yield of the reaction product in each example are measured, and results are shown in Table 6.

TABLE 6

| Catalyst | | Conversion of cyclopentanone (%) | Yield of cyclopentylamine (%) |
|---|---|---|---|
| Example 27 | 10% Co/$Al_2O_3$ | 80 | 25 |
| Example 28 | 10% Co/$TiO_2$ | 87 | 56 |
| Example 29 | 10% Co/$ZrO_2$ | 85 | 77 |

TABLE 6-continued

| Catalyst | | Conversion of cyclopentanone (%) | Yield of cyclopentylamine (%) |
|---|---|---|---|
| Example 30 | 10% Co/$CeO_2$ | 70 | 65 |
| Example 31 | 10% Co/$MoO_3$ | 76 | 74 |
| Example 32 | 10% Co/$SiO_2$ | 78 | 68 |
| Example 33 | 10% Co/C | 84 | 65 |
| Example 34 | 10% Co/$MgAl_2O_4$ | 66 | 42 |
| Example 35 | 10% Co/MgO | 76 | 50 |

The results in Table 6 show that the supported cobalt-based catalysts prepared from various carriers all have high catalytic activity.

Examples 36-59

In Examples 36-59, the core-shell Co@CoO catalyst is prepared, wherein cobalt nitrate serves as the cobalt source, sodium carbonate serves as the precipitant, the calcination temperature is 450° C., the reduction temperature is 300° C., the volume fraction of hydrogen in reducing gas is 10%, the flow rate of the reducing gas is 30 ml/min, and the reduction time is 2 h.

In Examples 36-59, the primary amine is prepared by catalysis of a cobalt-based catalyst, wherein 0.18 g of cyclopentanone serves as the reaction substrate, 0.02 g of Co@CoO-P-300 serves as the catalyst, and the batch reactor is used to obtain cyclopentylamine as the reaction product. Examples 36-59 differ from one another in the reaction media, the partial pressures of ammonia, the partial pressures of hydrogen, the reaction temperatures, and the reaction times. The conversion of the reaction substrate and the yield of the reaction product in each example are measured, and results are shown in Table 7.

TABLE 7

| | Reaction condition | Solvent | Conversion of cyclopentanone (%) | Yield of cyclopentylamine (%) |
|---|---|---|---|---|
| Example 36 | 90° C., 4 h, 0.3 MPa $NH_3$, 2 MPa $H_2$ | Methanol | 100 | 97.2 |
| Example 37 | 90° C., 4 h, 0.3 MPa $NH_3$, 2 MPa $H_2$ | Ethanol | 85 | 75 |
| Example 38 | 90° C., 4 h, 0.3 MPa $NH_3$, 2 MPa $H_2$ | Isopropanol | 90 | 85 |
| Example 39 | 90° C., 4 h, 0.3 MPa $NH_3$, 2 MPa $H_2$ | Ethylene glycol dimethyl ether | 85 | 79 |
| Example 40 | 90° C., 4 h, 0.3 MPa $NH_3$, 2 MPa $H_2$ | Toluene | 90 | 86 |
| Example 41 | 90° C., 4 h, 0.3 MPa $NH_3$, 2 MPa $H_2$ | P-xylene | 85 | 75 |
| Example 42 | 90° C., 4 h, 0.3 MPa $NH_3$, 2 MPa $H_2$ | Tetrahydrofuran | 75 | 68 |
| Example 43 | 90° C., 4 h, 0.4 MPa $NH_3$, 2 MPa $H_2$ | Methanol | 100 | 96 |
| Example 44 | 90° C., 4 h, 0.5 MPa $NH_3$, 2 MPa $H_2$ | Methanol | 100 | 96 |
| Example 45 | 90° C., 4 h, 0.6 MPa $NH_3$, 2 MPa $H_2$ | Methanol | 100 | 97 |
| Example 47 | 100° C., 2 h, 0.3 MPa $NH_3$, 2 MPa $H_2$ | Methanol | 100 | 90 |
| Example 48 | 110° C., 2 h, 0.3 MPa $NH_3$, 2 MPa $H_2$ | Methanol | 100 | 96 |
| Example 49 | 90° C., 4 h, 0.3 MPa $NH_3$, 1 MPa $H_2$ | Methanol | 100 | 96 |
| Example 50 | 90° C., 4 h, 0.3 MPa $NH_3$, 3 MPa $H_2$ | Methanol | 100 | 96 |
| Example 51 | 90° C., 4 h, 0.3 MPa $NH_3$, 4 MPa $H_2$ | Methanol | 100 | 95 |
| Example 53 | 90° C., 2 h, 0.3 MPa $NH_3$, 2 MPa $H_2$ | Methanol | 98 | 65 |

TABLE 7-continued

|  | Reaction condition | Solvent | Conversion of cyclopentanone (%) | Yield of cyclopentylamine (%) |
|---|---|---|---|---|
| Example 54 | 90° C., 3 h, 0.3 MPa $NH_3$, 2 MPa $H_2$ | Methanol | 100 | 90 |
| Example 55 | 90° C., 4 h, 2 MPa $H_2$ | 2M ammonia/methanol | 100 | 98 |
| Example 56 | 90° C., 4 h, 2 MPa $H_2$ | 2M ammonia/ethanol | 100 | 97 |
| Example 57 | 90° C., 4 h, 2 MPa $H_2$ | 2M ammonia/isopropanol | 100 | 96 |
| Example 58 | 90° C., 4 h, 2 MPa $H_2$ | 4M ammonia/methanol | 100 | 97 |
| Example 59 | 90° C., 4 h, 2 MPa $H_2$ | 7M ammonia/methanol | 100 | 96 |

The results in Table 7 show that the cobalt-based catalyst of the present disclosure can catalyze the reaction substrate to synthesize the primary amine at low temperature in a short time, with various reaction media, low partial pressure of ammonia, and low partial pressure of hydrogen, thereby improving the conversion of the reaction substrate and the yield of the product.

Examples 60-84

Examples 60-84 differ from one another in the methods for preparing the cobalt-based catalysts.

In Examples 60-84, the primary amine is prepared by catalysis of the cobalt-based catalyst, wherein cyclopentanone serves as the reaction substrate, methanol serves as the reaction medium, the feeding space velocity of cyclopentanone is 10-50 $h^{-1}$, the catalyst amount is 0.05 g, the flow rate of hydrogen is 20-50 ml/h, the partial pressure of hydrogen is 0.5-2 MPa, the flow rate of ammonia is 20-40 ml/h, the partial pressure of ammonia is 0.3-0.6 MPa, the temperature is 50° C.-200° C., and the continuous fixed bed reactor is used to obtain cyclopentylamine as the reaction product. The conversion of the reaction substrate and the yield of the reaction product in each example are measured, and results are shown in Table 8.

TABLE 8

|  | Catalyst | | | Conversion of | Yield of |
|---|---|---|---|---|---|
|  |  | Cobalt source | Precipitant | Reduction temperature | cyclopentanone (%) | cyclopentylamine (%) |
| Example 60 | Co@CoO-P-275 | cobalt nitrate | sodium carbonate | 275° C. | 100 | 51 |
| Example 61 | Co@CoO-P-300 | cobalt nitrate | sodium carbonate | 300° C. | 100 | 81 |
| Example 62 | Co@CoO-P-350 | cobalt nitrate | sodium carbonate | 350° C. | 100 | 45 |
| Example 63 | Co@CoO-P-400 | cobalt nitrate | sodium carbonate | 400° C. | 88 | 50 |
| Example 64 | Co@CoO-P-300 | cobalt acetate | sodium carbonate | 300° C. | 80 | 45 |
| Example 65 | Co@CoO-P-300 | cobalt chloride | sodium carbonate | 300° C. | 75 | 48 |
| Example 66 | Co@CoO-P-300 | cobalt carbonyl | sodium carbonate | 300° C. | 85 | 34 |
| Example 67 | Co@CoO-P-300 | cobalt nitrate | sodium hydroxide | 300° C. | 61 | 40 |
| Example 68 | Co@CoO-P-300 | cobalt nitrate | sodium bicarbonate | 300° C. | 80 | 37 |
| Example 69 | Co@CoO-P-300 | cobalt nitrate | ammonium carbonate | 300° C. | 65 | 38 |
| Example 70 | Co@CoO-P-300 | cobalt nitrate | ammonium bicarbonate | 300° C. | 61 | 42 |
| Example 71 | Co@CoO-P-300 | cobalt nitrate | urea | 300° C. | 54 | 38 |
| Example 72 | Co@CoO-D-275 | cobalt nitrate | None | 275° C. | 100 | 62 |
| Example 73 | Co@CoO-D-300 | cobalt nitrate | None | 300° C. | 100 | 54 |
| Example 74 | Co@CoO-D-350 | cobalt nitrate | None | 350° C. | 100 | 41 |
| Example 75 | Co@CoO-D-400 | cobalt nitrate | None | 400° C. | 88 | 46 |
| Example 76 | 10% Co/$Al_2O_3$ | cobalt chloride | None | 300° C. | 90 | 62 |

TABLE 8-continued

| | Catalyst | | | Conversion of cyclopentanone (%) | Yield of cyclopentylamine (%) |
|---|---|---|---|---|---|
| | Cobalt source | Precipitant | Reduction temperature | | |
| Example 77 | 10% Co/MgO | cobalt chloride | None | 300° C. | 88 | 71 |
| Example 78 | 10% Co/TiO$_2$ | cobalt chloride | None | 300° C. | 79 | 60 |
| Example 79 | 10% Co/ZrO$_2$ | cobalt chloride | None | 300° C. | 68 | 36 |
| Example 80 | 10% Co/CeO$_2$ | cobalt chloride | None | 300° C. | 64 | 51 |
| Example 81 | 10% Co/MoO$_3$ | cobalt chloride | None | 300° C. | 84 | 61 |
| Example 82 | 10% Co/SiO$_2$ | cobalt chloride | None | 300° C. | 76 | 62 |
| Example 83 | 10% Co/C | cobalt chloride | None | 300° C. | 80 | 70 |
| Example 84 | 10% Co/MgAl$_2$O$_4$ | cobalt chloride | None | 300° C. | 71 | 63 |

The results in Table 8 show that the cobalt-based catalysts prepared through different methods all can well catalyze carbonyl compounds to synthesize the primary amine.

Examples 85-102

Examples 85-102 differ from one another in the methods for preparing the cobalt-based catalysts.

In Examples 85-102, the primary amine is prepared by catalysis of the cobalt-based catalyst, wherein 0.18 g of cyclopentanol serves as the reaction substrate, the catalyst amount is 0.04 g, 5 ml of p-xylene serves as the reaction medium, the partial pressure of ammonia is 0.6 MPa, the partial pressure of hydrogen is 0.2 MPa, the reaction temperature is 180° C., the reaction time is 24 h, and the batch reactor is used to obtain cyclopentylamine as the reaction product. The conversion of the reaction substrate and the yield of the reaction product in each example are measured, and results are shown in Table 9.

TABLE 9

| Catalyst | | Conversion of cyclopentanol (%) | Yield of cyclopentylamine (%) |
|---|---|---|---|
| Example 85 | Co@CoO-P-250 | 60 | 57 |
| Example 86 | Co@CoO-P-275 | 76 | 74 |
| Example 87 | Co@CoO-P-300 | 100 | 90 |
| Example 88 | Co@CoO-P-350 | 80 | 75 |
| Example 89 | Co@CoO-P-400 | 40 | 36 |
| Example 90 | Co@CoO-D-250 | 36 | 32 |
| Example 91 | Co@CoO-D-275 | 57 | 53 |
| Example 92 | Co@CoO-D-300 | 34 | 30 |
| Example 93 | Co@CoO-D-350 | 25 | 21 |
| Example 94 | 10% Co/Al$_2$O$_3$ | 60 | 40 |
| Example 95 | 10% Co/TiO$_2$ | 55 | 45 |
| Example 96 | 10% Co/ZrO$_2$ | 71 | 35 |
| Example 97 | 10% Co/CeO$_2$ | 60 | 41 |
| Example 98 | 10% Co/MoO$_3$ | 63 | 55 |
| Example 99 | 10% Co/SiO$_2$ | 43 | 20 |
| Example 100 | 10% Co/C | 62 | 50 |

TABLE 9-continued

| Catalyst | | Conversion of cyclopentanol (%) | Yield of cyclopentylamine (%) |
|---|---|---|---|
| Example 101 | 10% Co/MgAl$_2$O$_4$ | 53 | 41 |
| Example 102 | 10% Co/MgO | 82 | 71 |

The results in Table 9 show that the cobalt-based catalysts prepared through different methods all can well catalyze alcohol compounds to synthesize the primary amine.

Examples 103-122

In Examples 103-122, the core-shell Co@CoO catalyst is prepared, wherein cobalt nitrate serves as the cobalt source, sodium carbonate serves as the precipitant, the calcination temperature is 450° C., the reduction temperature is 300° C., the volume fraction of hydrogen in the reducing gas is 10%, the flow rate of the reducing gas is 30 ml/min, and the reduction time is 2 h.

In Examples 103-122, the primary amine is prepared by catalysis of the cobalt-based catalyst, wherein 0.02 g of Co@CoO-P-300 serves as the catalyst, 5 ml of methanol serves as the reaction medium, the partial pressure of ammonia is 0.3 MPa, the partial pressure of hydrogen is 2 MPa, the reaction temperature is 100° C., the reaction time is 4 h, and the batch reactor is used. Examples 103-111 differ from one another in the reaction substrates, and particularly, the reaction substrates in Examples 103-111 are acetone, propionaldehyde, butanone, butyraldehyde, 2-pentanone, valeraldehyde, 4-heptanone, octanal, 2-octanone, 5-nonanone, benzaldehyde, phenylacetaldehyde, phenylpropionaldehyde, acetophenone, 4-chloroacetophenone, 2-bromoacetophenone, 2-methoxypropiophenone, 2-naphthaldehyde, 4-hydroxyphenylacetophenone, 4-methoxybenzaldehyde, and benzophenone, separately. The conversion of the reaction substrate and the yield of a reaction product in each example are measured, and results are shown in Table 10.

TABLE 10

|  | Catalyst | Conversion of substrate (%) | Yield of primary amine (%) |
|---|---|---|---|
| Example 103 acetone | Co@CoO-P-300 | 100 | 90 |
| Example 104 propionaldehyde | Co@CoO-P-300 | 100 | 95 |
| Example 105 butyraldehyde | Co@CoO-P-300 | 100 | 96 |
| Example 106 2-pentanone | Co@CoO-P-300 | 100 | 93 |
| Example 107 4-heptanone | Co@CoO-P-300 | 96 | 90 |
| Example 108 octanal | Co@CoO-P-300 | 90 | 86 |
| Example 109 2-octanone | Co@CoO-P-300 | 80 | 75 |
| Example 110 3-octanone | Co@CoO-P-300 | 80 | 73 |
| Example 111 5-nonanone | Co@CoO-P-300 | 85 | 74 |
| Example 112 benzaldehyde | Co@CoO-P-300 | 90 | 85 |
| Example 113 phenylacetaldehyde | Co@CoO-P-300 | 100 | 70 |
| Example 114 phenylpropionaldehyde | Co@CoO-P-300 | 96 | 80 |
| Example 115 acetophenone | Co@CoO-P-300 | 85 | 76 |
| Example 116 4-chloroacetophenone | Co@CoO-P-300 | 90 | 85 |
| Example 117 2-bromoacetophenone | Co@CoO-P-300 | 80 | 74 |
| Example 118 2-methoxypropiophenone | Co@CoO-P-300 | 95 | 82 |
| Example 119 2-naphthaldehyde | Co@CoO-P-300 | 80 | 75 |
| Example 120 4-hydroxyphenylacetophenone | Co@CoO-P-300 | 85 | 76 |
| Example 121 4-methoxybenzaldehyde | Co@CoO-P-300 | 100 | 94 |
| Example 122 benzophenone | Co@CoO-P-300 | 75 | 65 |

The results in Table 10 show that the cobalt-based catalyst in the present disclosure can catalyze aliphatic aldehydes and/or ketones and aromatic aldehydes and/or ketones to synthesize the primary amine with a wide range of applicable substrates, so that the synthetic routes of primary amines can be increased.

Examples 123-128

In Examples 123-128, the core-shell Co@CoO catalyst is prepared, wherein cobalt nitrate serves as the cobalt source, sodium carbonate serves as the precipitant, the calcination temperature is 450° C., the reduction temperature is 300° C., the volume fraction of hydrogen in the reducing gas is 10%, the flow rate of the reducing gas is 30 ml/min, and the reduction time is 2 h.

In Examples 123-128, the primary amine is prepared by catalysis of the cobalt-based catalyst, wherein 0.04 g of Co@CoO-P-300 serves as the catalyst, 5 ml of p-xylene serves as the reaction medium, the partial pressure of ammonia is 0.6 MPa, the partial pressure of hydrogen is 0.2 MPa, the reaction temperature is 180° C., the reaction time is 24 h, and the batch reactor is used. Examples 123-128 differ from one another in the reaction substrates, and particularly, the reaction substrates in Examples 123-128 are propanol, n-butanol, cyclopentanol, cyclohexanol, 1-octanol, and benzyl alcohol, separately. The conversion of the reaction substrate and the yield of a reaction product in each example are measured, and results are shown in Table 11.

The results in Table 11 show that the cobalt-based catalyst in the present disclosure can catalyze aliphatic alcohols and aromatic alcohols to synthesize the primary amine with a wide range of applicable substrates, so that the synthetic routes of primary amines can be increased.

Examples 129-153

In Examples 129-153, the core-shell Co@CoO catalyst is prepared, wherein cobalt nitrate serves as the cobalt source, sodium carbonate serves as the precipitant, the calcination temperature is 450° C., the reduction temperature is 300° C., the volume fraction of hydrogen in the reducing gas is 10%, the flow rate of the reducing gas is 30 ml/min, and the reduction time is 2 h.

In Examples 129-153, the primary amine is prepared by catalysis of the cobalt-based catalyst, wherein 0.18 g of cyclopentanone serves as the reaction substrate, 0.02 g of Co@CoO-P-300 serves as the catalyst, 5 ml of methanol serves as the reaction medium, the partial pressure of ammonia is 0.3 MPa, the partial pressure of hydrogen is 2 MPa, the reaction temperature is 90° C., the reaction time is 2 h, and the batch reactor is used to obtain cyclopentylamine as the reaction product. In Examples 129-153, the core-shell Co@CoO catalyst is recycled. Particularly, after the previous experiment, the catalyst is washed three times with methanol, dried in an oven of 60° C., and used in the next experiment again. The conversion of the reaction substrate and the yield of the reaction product in each example are measured, and results are shown in Table 12.

TABLE 11

|  | Substrate | Catalyst | Conversion of substrate (%) | Yield of primary amine (%) |
|---|---|---|---|---|
| Example 123 | propanol | Co@CoO-P-300 | 100 | 90 |
| Example 124 | N-butanol | Co@CoO-P-300 | 100 | 89 |
| Example 125 | cyclopentanol | Co@CoO-P-300 | 100 | 91 |
| Example 126 | cyclohexanol | Co@CoO-P-300 | 100 | 90 |
| Example 127 | 1-octanol | Co@CoO-P-300 | 100 | 88 |
| Example 128 | benzyl alcohol | Co@CoO-P-300 | 100 | 92 |

TABLE 12

|  | Recycling time | Catalyst | Conversion of cyclopentanone (%) | Yield of cyclopentylamine (%) |
|---|---|---|---|---|
| Example 129 | 1 | Co@CoO-P-300 | 98 | 65 |
| Example 130 | 2 | Co@CoO-P-300 | 100 | 96 |
| Example 131 | 3 | Co@CoO-P-300 | 100 | 97 |
| Example 132 | 4 | Co@CoO-P-300 | 100 | 96 |
| Example 133 | 5 | Co@CoO-P-300 | 100 | 95 |
| Example 134 | 6 | Co@CoO-P-300 | 100 | 95 |
| Example 135 | 7 | Co@CoO-P-300 | 100 | 96 |

TABLE 12-continued

| | Recycling time | Catalyst | Conversion of cyclopentanone (%) | Yield of cyclopentylamine (%) |
|---|---|---|---|---|
| Example 136 | 8 | Co@CoO-P-300 | 100 | 96 |
| Example 137 | 9 | Co@CoO-P-300 | 100 | 96 |
| Example 138 | 10 | Co@CoO-P-300 | 100 | 97 |
| Example 139 | 11 | Co@CoO-P-300 | 100 | 95 |
| Example 140 | 12 | Co@CoO-P-300 | 100 | 96 |
| Example 141 | 13 | Co@CoO-P-300 | 100 | 96 |
| Example 142 | 14 | Co@CoO-P-300 | 100 | 96 |
| Example 143 | 15 | Co@CoO-P-300 | 100 | 97 |
| Example 144 | 16 | Co@CoO-P-300 | 100 | 96 |
| Example 145 | 17 | Co@CoO-P-300 | 100 | 96 |
| Example 146 | 18 | Co@CoO-P-300 | 100 | 96 |
| Example 147 | 19 | Co@CoO-P-300 | 100 | 95 |
| Example 148 | 20 | Co@CoO-P-300 | 100 | 96 |
| Example 149 | 21 | Co@CoO-P-300 | 100 | 95 |
| Example 150 | 22 | Co@CoO-P-300 | 100 | 95 |
| Example 151 | 23 | Co@CoO-P-300 | 100 | 92 |
| Example 152 | 24 | Co@CoO-P-300 | 100 | 90 |
| Example 153 | 25 | Co@CoO-P-300 | 100 | 88 |

The results in Table 12 show that the cobalt-based catalyst is magnetic, which can facilitate separation and recycling of the catalyst, and thus has a good industrial application prospect.

Comparative Examples 1-6

Catalysts used in Comparative Examples 1-6 are copper-based catalysts, and the copper-based catalysts in Comparative Examples 1-6 are prepared in the same manner as the cobalt-based catalysts in Examples 8-13, respectively. The primary amines are prepared by catalysis of the copper-based catalysts in Comparative Examples 1-6 in the same manner as the primary amines prepared by catalysis of the cobalt-based catalysts in Examples 8-13, respectively. Conversions of reaction substrates and yields of reaction products in Comparative Examples 1-6 are measured, and results are shown in Table 13.

TABLE 13

| | Catalyst | Conversion of cyclopentanone (%) | Yield of cyclopentylamine (%) |
|---|---|---|---|
| Comparative Example 1 | Cu@CuO-P-225 | 40 | 0 |
| Comparative Example 2 | Cu@CuO-P-250 | 41 | 5 |
| Comparative Example 3 | Cu@CuO-P-275 | 60 | 7 |
| Comparative Example 4 | Cu@CuO-P-300 | 55 | 10 |
| Comparative Example 5 | Cu@CuO-P-350 | 25 | 0 |
| Comparative Example 6 | Cu@CuO-P-400 | 27 | 0 |

By comparing Examples 8-13 with Comparative Examples 1-6, it can be seen that the cobalt-based catalyst has higher catalytic activity, selectivity and stability.

Comparative Example 7-8

Comparative Examples 7-8 differ from Examples 8-13 only in the reduction temperatures, 90° C. in Comparative Example 7 and 410° C. in Comparative Example 8, separately. Conversions of reaction substrate and yields of reaction product in Comparative Examples 7-8 are measured, and results are shown in Table 14.

TABLE 14

| | Catalyst | Conversion of cyclopentanone (%) | Yield of cyclopentylamine (%) |
|---|---|---|---|
| Comparative Example 7 | Cu@CuO-P-90 | 20 | 0 |
| Comparative Example 8 | Cu@CuO-P-410 | 25 | 0 |

By comparing Examples 8-13 with Comparative Examples 7-8, it can be seen that the cobalt-based catalyst prepared at the reduction temperature of 100-400° C. has higher catalytic activity.

Comparative Examples 9-10

Comparative Examples 9-10 differ from Example 36 only in the reduction temperatures, 65° C. in Comparative Example 9 and 210° C. in Comparative Example 10, separately. Conversion of reaction substrate and yields of reaction product in Comparative Examples 9-10 are measured, and results are shown in Table 15.

TABLE 15

| | Reaction condition | Solvent | Conversion of cyclopentanone (%) | Yield of cyclopentylamine (%) |
|---|---|---|---|---|
| Comparative Example 9 | 65° C., 4 h, 0.3 MPa $NH_3$, 2 MPa $H_2$ | Methanol | 25 | 0 |
| Comparative Example 10 | 210° C., 4 h, 0.3 MPa $NH_3$, 2 MPa $H_2$ | Methanol | 100 | 97 |

By comparing Example 36 with Comparative Examples 9-10, it can be seen that when the reaction for synthesizing primary amines is catalyzed by the cobalt-based catalysts, the catalytic effect will be better if the reaction temperature is higher than or equal to 70° C. However, the catalytic effect is not significantly improved if the reaction temperature is higher than 200° C. In consideration of the industrial cost, it is feasible to control the reaction temperature at 70-200° C., so as to achieve good catalytic activity and save on the industrial cost.

The method for efficiently synthesizing primary amines provided by the present disclosure has high catalytic activity, the method can realize the reductive amination of carbonyl compounds and the hydrogen-borrowing amination of alcohol compounds at low temperatures in a short time to obtain the primary amines with high yield, and is applicable to a wide range of substrates. The obtained primary amines can be used as raw materials with high extra value for producing polymers, medicines, dyes and surfactants. Further, the cobalt-based catalyst has a good industrial application prospect because it is magnetic which can facilitate separation and recycling of the catalyst. Moreover, the inexpensive cobalt-based catalyst can significantly reduce industrialization cost.

Those of ordinary skill in the art shall understand that the discussion of any example above is exemplary only and is not intended to imply that the scope of the present disclosure (including claims) is limited to these examples. It is within the spirit of the present disclosure that the technical features of the examples above or different examples may also be combined, steps may be implemented in any order, and many other variations may be made to different aspects of the examples described above of the present disclosure, which are not provided in detail for the sake of brevity.

The examples of the present disclosure are intended to cover all such alternatives, modifications, and variations which fall within the broad scope of appended claims. Accordingly, any omissions, modifications, equivalents, improvements, etc., which come within the spirit and principles of the examples of the present disclosure shall all fall within the scope of protection of the present disclosure.

What is claimed is:

1. A method for efficiently synthesizing primary amines, comprising using carbonyl compounds or alcohol compounds as reaction substrate, liquid ammonia or alcohol solutions of ammonia as nitrogen source, and hydrogen as hydrogen source, and reacting in reaction medium catalyzed by a cobalt-based catalyst to obtain the primary amines.

2. The method according to claim 1, wherein the carbonyl compounds comprise aliphatic aldehydes and/or ketones and aromatic aldehydes and/or ketones.

3. The method according to claim 1, wherein the alcohol compounds comprise aliphatic alcohols and aromatic alcohols.

4. The method according to claim 1, wherein the alcohol solutions of ammonia comprise at least one selected from ammonia/methanol, ammonia/ethanol, and ammonia/isopropanol.

5. The method according to claim 1, wherein the reaction medium comprises organic solvents, the organic solvents comprising at least one selected from methanol, ethanol, isopropanol, ethylene glycol dimethyl ether, tetrahydrofuran, toluene and p-xylene.

6. The method according to claim 1, wherein a mass ratio of the reaction substrate to the cobalt-based catalyst is 1:(0.01-2); and/or
   a mass ratio of the reaction substrate to the reaction medium is 1:(1-60); and/or
   a concentration of the alcohol solution of ammonia is 2 M-7 M; and/or
   a pressure of the gasified liquid ammonia is 0.1-1 MPa; and/or
   a pressure of the hydrogen is 0.5-5 MPa; and/or
   a reaction temperature is 70-200° C.; and/or
   a reaction time is 0.5-25 h.

7. The method according to claim 1, wherein the cobalt-based catalyst comprises a core-shell Co@CoO catalyst.

8. The method according to claim 7, wherein the core-shell Co@CoO catalyst comprises a core of cobalt and a shell of cobalt monoxide containing oxygen vacancies.

9. The method according to claim 7, wherein a method for preparing the core-shell Co@CoO catalyst comprises preparing a precursor, and then optionally reducing the precursor in a reducing gas to obtain the core-shell Co@CoO catalyst.

10. The method according to claim 9, wherein a volume fraction of hydrogen in the reducing gas is 5-30%; and/or
    a flow rate of the reducing gas is 10-100 ml/min; and/or
    a reduction temperature is 100-400° C.; and/or
    a reduction time is 1-6 h.

11. The method according to claim 9, wherein a method for preparing the precursor comprises preparing a precipitate from a cobalt source and a precipitant by a precipitation method, and then optionally calcining the precipitate to obtain the precursor;
    the cobalt source comprises at least one of salts, esters and complexes containing Co element; and/or
    the precipitant comprises at least one of amides, alkalis and salts capable of co-precipitated with the cobalt source; and/or
    the calcination temperature is 400-450° C.

12. The method according to claim 9, wherein a method for preparing the precursor comprises preparing the precursor from a cobalt source by a high-temperature thermal decomposition method;
    the cobalt source comprises at least one of salts, esters and complexes containing Co element; and/or
    the conditions of the high-temperature thermal decomposition method comprise: a calcination temperature of 300-600° C.

13. The method according to claim 1, wherein the cobalt-based catalyst comprises a supported cobalt-based catalyst.

14. The method according to claim 13, wherein a carrier of the supported cobalt-based catalyst comprises at least one of metal oxides, $SiO_2$, and activated carbon.

15. The method according to claim 14, wherein the metal oxides comprise at least one of IIIA-group metal oxides, IIA-group metal oxides, IVB-group metal oxides, lanthanide metal oxides and VIB-group metal oxides.

16. The method according to claim 13, wherein a method for preparing the supported cobalt-based catalyst comprises preparing a precursor, and then optionally reducing the precursor in a reducing gas to obtain the supported cobalt-based catalyst.

17. The method according to claim 16, wherein a volume fraction of hydrogen in the reducing gas is 5-30%; and/or
    a flow rate of the reducing gas is 10-100 ml/min; and/or
    a reduction temperature is 100-400° C.; and/or
    a reduction time is 1-6 h.

18. The method according to claim 16, wherein a method for preparing the precursor comprises co-precipitating a cobalt source with a carrier precursor to prepare a precipitate, and then optionally calcining the precipitate to obtain the precursor;
    the cobalt source comprises at least one of salts, esters and complexes containing Co element; and/or
    the carrier precursor comprises at least one of IIIA-group metal salts, IIA-group metal salts, IVB-group metal salts, lanthanide metal salts, and VIB-group metal salts; and/or
    the calcination temperature is 350-450° C.

19. The method according to claim 16, wherein a method for preparing the precursor comprises obtaining a carrier, then supporting a cobalt source on the carrier by an incipient-wetness impregnation method, a wet impregnation method or a precipitation deposition method, and optionally calcining;
    the cobalt source comprises at least one of salts, esters and complexes containing Co element; and/or
    the calcination temperature is 350-450° C.

20. The method according to claim 14, wherein the metal oxides are selected from at least one of $Al_2O_3$, MgO, $MgAl_2O_4$, $TiO_2$, $ZrO_2$, $CeO_2$, and $MoO_3$.

* * * * *